United States Patent [19]

Brown et al.

[11] Patent Number: 4,604,093
[45] Date of Patent: Aug. 5, 1986

[54] APPARATUS AND METHOD FOR ADMINISTERING MULTIPLE FLUID INFUSIONS

[75] Inventors: Eric W. Brown, Redondo Beach; Henry T. Tai, Pacific Palisades, both of Calif.

[73] Assignee: I-Flow Corporation, Redondo Beach, Calif.

[21] Appl. No.: 619,847

[22] Filed: Jun. 12, 1984

[51] Int. Cl.⁴ ............................................. A61M 5/14
[52] U.S. Cl. ..................................... 604/248; 604/81; 137/625.11
[58] Field of Search ..................... 604/32, 56, 65, 67, 604/80–81, 248; 137/625.11, 625.16, 625.41

[56] References Cited

U.S. PATENT DOCUMENTS

| D. 271,421 | 11/1983 | Fetterman . |
| 825,370 | 7/1906 | Zurbuch . |
| 1,228,469 | 6/1917 | Mueller . |
| 1,469,612 | 10/1923 | Bahr . |
| 2,261,213 | 11/1941 | Bierman . |
| 3,012,752 | 12/1961 | Buck ................................. 604/248 |
| 3,057,350 | 10/1962 | Cowley . |
| 3,057,370 | 10/1962 | Hamilton . |
| 3,115,896 | 12/1963 | Roberts et al. . |
| 3,185,179 | 5/1965 | Harautuneian . |
| 3,508,582 | 4/1970 | Aulisa . |
| 3,618,637 | 11/1971 | Santomieri . |
| 3,678,960 | 7/1972 | Leibinsohn . |
| 3,774,604 | 11/1973 | Danielsson . |
| 3,783,900 | 1/1974 | Waldbillig . |
| 3,834,372 | 9/1974 | Turney . |
| 3,957,082 | 5/1976 | Fuson et al. . |
| 4,048,474 | 9/1977 | Oleson . |
| 4,094,318 | 6/1978 | Burke et al. . |
| 4,111,198 | 9/1978 | Marx et al. . |
| 4,121,584 | 10/1978 | Turner et al. . |
| 4,191,183 | 3/1980 | Mendelson . |
| 4,191,213 | 3/1980 | Döling et al. ................... 137/625.11 |
| 4,196,730 | 4/1980 | Wilson . |
| 4,207,871 | 6/1980 | Jenkins . |
| 4,215,476 | 8/1980 | Armstrong ........................... 604/32 |
| 4,219,021 | 8/1980 | Fink . |
| 4,219,022 | 8/1980 | Genese . |
| 4,256,103 | 3/1981 | Mylrea . |
| 4,257,416 | 3/1981 | Prager . |
| 4,258,712 | 3/1981 | Harms et al. . |
| 4,261,356 | 4/1981 | Turner et al. . |
| 4,265,240 | 5/1981 | Jenkins . |
| 4,291,692 | 9/1981 | Bowman et al. . |
| 4,298,026 | 11/1981 | Ambers . |
| 4,316,460 | 2/1982 | Genese et al. . |
| 4,324,238 | 4/1982 | Genese et al. . |
| 4,333,454 | 6/1982 | Hargest, III . |
| 4,391,598 | 7/1983 | Thompson . |
| 4,407,660 | 10/1983 | Nevens et al. . |
| 4,425,113 | 1/1984 | Bilstad . |
| 4,428,745 | 1/1984 | Williams . |
| 4,430,074 | 2/1984 | Mooring . |
| 4,512,764 | 4/1985 | Wunsch ................................. 604/80 |

FOREIGN PATENT DOCUMENTS 2855713  6/1980  Fed. Rep. of Germany ........ 604/67

OTHER PUBLICATIONS

Ivent Corp., ad from *Medical Electronics and Equipment News*, Aug. 1984, vol. 24, No. 4.
Hutchinson, Administration of Fat Emulsions, *American Journal of Nursing*, Feb., 1982.

Primary Examiner—C. Fred Rosenbaum
Assistant Examiner—Michelle N. Lester
Attorney, Agent, or Firm—Robert M. Asher

[57] ABSTRACT

A valve is disclosed which includes a hollow cylindrical housing having a plurality of input sites and a rotary core member having an output pasageway. The input sites which are not in communication with the output passageway are sealed. The valve may also include a primary input site connected to a conduit surrounding the rotary core member of the valve. The valve is demountable on a control apparatus for performing a method of administering a plurality of fluids intravenously to a patient. According to the method of the present invention, a neutral solution is provided in between each of the other different fluid solutions being infused into the patient. The control apparatus of the present invention may be programmed to automatically provide the patient with a prescribed amount of each fluid solution through the catheter tube.

25 Claims, 9 Drawing Figures

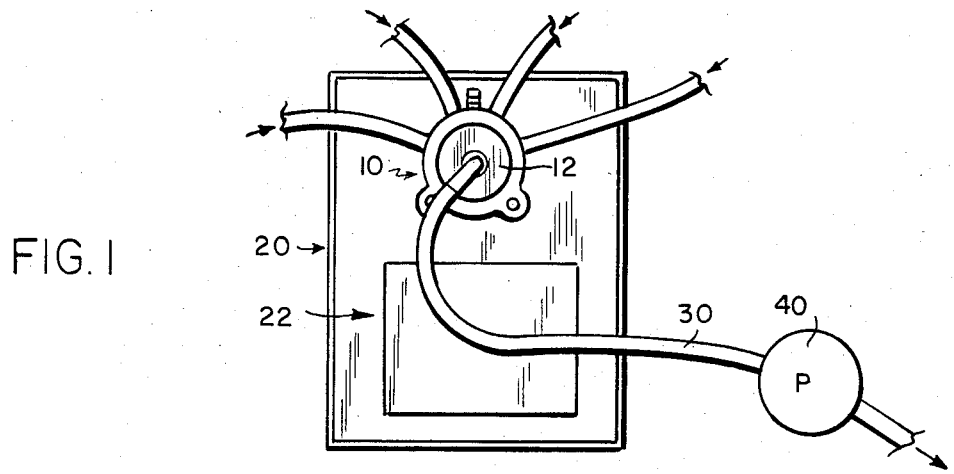
FIG. 1
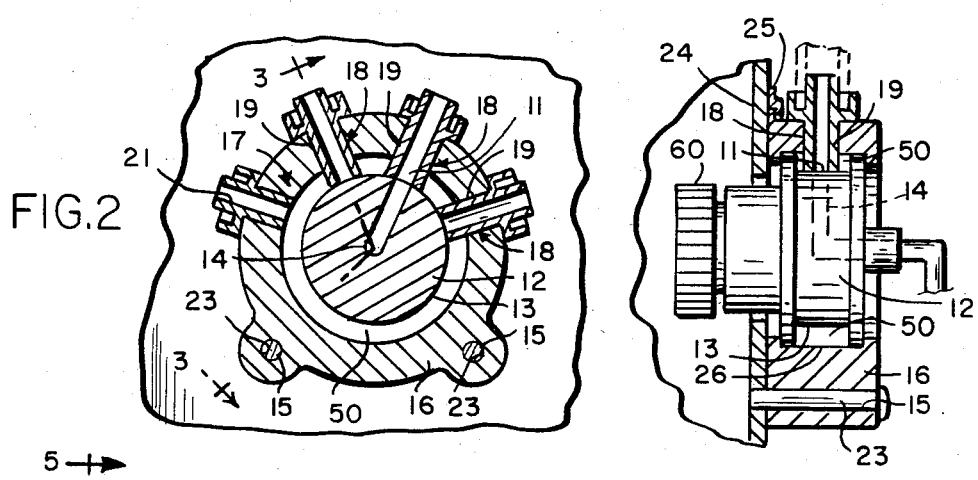
FIG. 2
FIG. 3
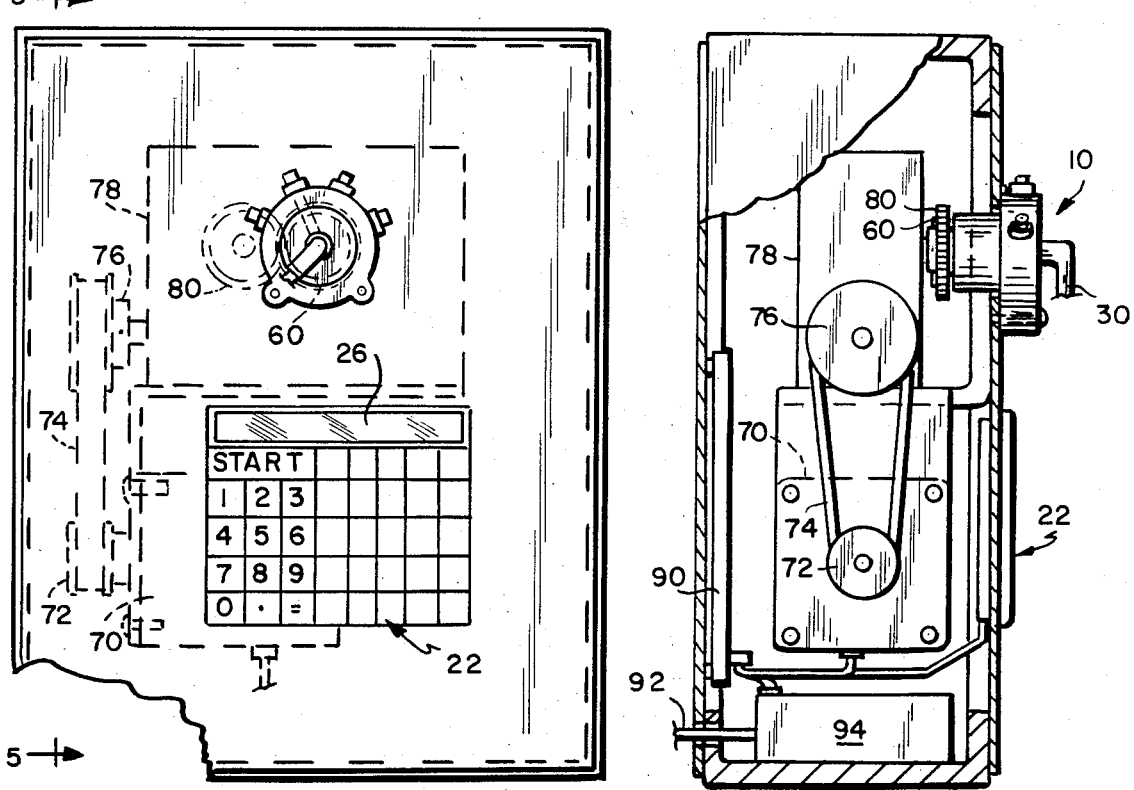
FIG. 4
FIG. 5

APPARATUS AND METHOD FOR ADMINISTERING MULTIPLE FLUID INFUSIONS

BACKGROUND OF THE INVENTION

This invention relates to the administration of multiple fluid infusions.

There are many applications for which there is a need for a device which can intravenously administer a plurality of drugs. One such application is the use of chemotherapy to treat diseases such as cancer. Another application is hyperalimentation where several nutritional solutions are intravenously administered to a patient.

Attempts at providing more advanced chemotherapy regimens involving the intravenous administration of a multiplicity of drug solutions are being inhibited by a lack of equipment to simplify such a procedure. Very often if different drug solutions are used, they are administered by using a separate catheter tube for each drug. A separate infusion pump would be used on each individual catheter tube line and the tube would deliver the fluid solution into the patient through its respective intravascular access needle. A patient must pay for each catheter set and must rent a pump for use with each catheter tube. Therefore, it is costly to use multiple catheter tubes and pumps. A further problem would be the discomfort and complications involved in applying and maintaining several vascular access sites in a single patient.

Some physicians administer chemotherapy treatments with a plurality of drug solutions by mixing the solutions together and feeding the mixture into the patient through a single catheter set and pump. If the different drug solutions are compatible, they can be mixed and delivered through a single catheter. Unfortunately, there are only a limited number of drug combinations which can be used in this manner. Many drugs cannot be mixed together prior to infusion. Some drugs react to neutralize one another. Other drugs react to form precipitates which may block the catheter tube or possibly cause an embolism in the patient.

Because of these problems, it is desirable to keep the multiple fluid solutions separated. Attention is directed to the inventors' copending patent application entitled "Method for Sequential Intravenous Infusion of Multiple Fluids", which shares the same filing date and assignee as the present application. The method described in the copending application enables the use of a single catheter tube for multiple drug infusions. In order to deliver a plurality of fluid solutions separately through a single catheter tube, a valve is generally required. The valve must be sterile to perform this application; thus a disposable valve would be preferable. There are some known valves which may be manually adjusted. For example, a rotary mixing valve, invented by Santomieri, is described in U.S. Pat. No. 3,618,637. However, this valve provides a primary fluid which is commingled with selected secondary fluid solutions and if the valve is rotated to switch between secondary inputs, fluid flow will be interrupted.

SUMMARY OF THE INVENTION

This invention is directed to a method and apparatus for administering multiple fluid infusions. The apparatus includes a valve for selectively communicating any one of a plurality of available fluid solutions with an output tube. The valve includes a hollow cylindrical housing having a primary input site and a plurality of secondary input sites. There is a core member engaged within the hollow cylindrical housing which has an output passageway for coupling the inputs with the output tube. Means are provided around the circumference of the core member for sealing off the input sites which are not in communication with the output passageway through an access hole in the circumference. The primary input site is connected via a conduit with the circumference of the core member so that the fluid provided through the primary input site is in communication with the output passageway whenever the access hole is aligned between two adjacent secondary input sites.

The method of the present invention for administering multiple fluid solutions to a patient begins by providing a sterile valve having a single output and a plurality of inputs. A neutral solution is connected through one input of the valve and the remainder of the inputs are connected to one of several fluid solutions. A catheter tube is connected between the output of the valve and the patient. A pump is coupled to the catheter tube for delivering fluid through the tube at a predetermined speed. The drug regimen is delivered by alternately switching the valve between the input providing the neutral solution and one of the other inputs connected to the drug solutions. The use of this method and valve advantageously avoids a substantial mixing of the drug solutions prior to injection into the patient. Thus, physicians will be given new flexibility in their choice of intravenous drug combinations for use in chemotherapy or other similar treatments.

The apparatus for performing the method of the present invention employs a valve with several input sites and a single output site through an output passageway in a rotary core member. A motor is provided for turning the rotary core member to select the connection between an input and the output passageway. A catheter tube is connected to the valve and a pump is coupled with the catheter tube for delivering fluid through the tube at a predetermined speed. A preprogrammed microprocessor is provided for controlling the motor to provide selected drug solutions to the catheter tube in a predetermined sequence for predetermined time intervals.

It is an object of the present invention to provide a sterile disposable valve for selectively communicating with one of several fluid solutions for input through a catheter tube. It is a further object of the present invention to provide an automatically controlled apparatus for selectively communicating a catheter tube with a selection of fluid solutions. An advantage of the automatic control of the present invention is that it may be programmed to handle any regimen as prescribed.

A still further object of the present invention is to provide a valve having a primary input that is accessible through a conduit between the input sites for the plurality of fluid solutions. This advantageously allows simple implementation of a drug regimen which alternates the provision of a neutral solution with a selected sequence of fluid solutions, since the valve does not need to switch repeatedly its output into alignment with the primary input site. The objective of this neutral solution is to substantially isolate the plurality of fluid solutions that are fed into the catheter tube.

Other objects and advantages of the invention will become apparent during the following description of the presently preferred embodiment of the invention taken in conjunction with the drawings.

BRIEF DESCRIPTION OF THE DRAWINGS

FIG. 1 is an elevational view of an apparatus of the present invention for administering multiple fluid infusions.

FIG. 2 is a cross-sectional view of a valve of the present invention.

FIG. 3 is a sectional view taken along lines 3—3 of the valve in FIG. 2.

FIG. 4 is another elevational view of the apparatus of FIG. 1.

FIG. 5 is a sectional view of the apparatus of FIG. 4 taken along lines 5—5.

DETAILED DESCRIPTION OF THE PREFERRED EMBODIMENT

Figure 6:
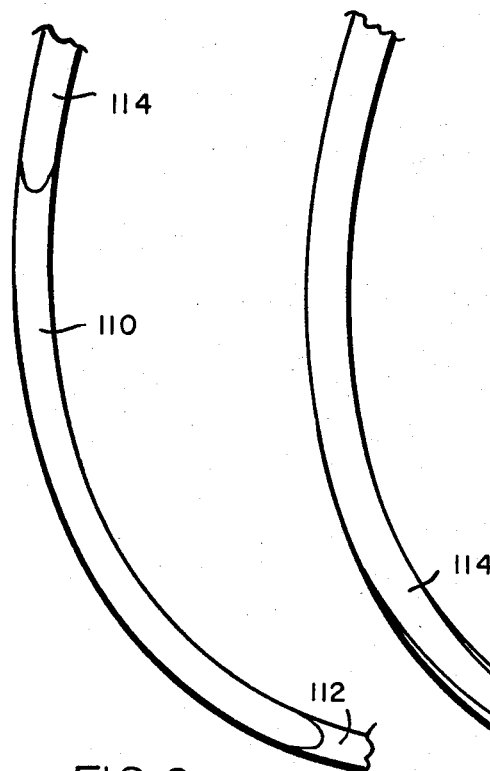
FIG. 6 is a sectional view of the catheter tube shown in FIG. 1 demonstrating the method of the present invention.

Turning now to the drawings, FIG. 1 is a simplified elevational view of the apparatus of the present invention. A valve 10 is mounted on control apparatus 20. The valve 10 is shown receiving four inputs from intravenous fluid solution sources. The valve 10 includes rotary core member 12. The rotary core member 12 has an output passageway 14 which is connected to a catheter tube 30 for delivering fluid to a patient. A pump 40 is coupled to the catheter tube for delivering the fluid at a predetermined speed. The pump 40 which is used with the present invention may be any conventional type of infusion pump. The presently preferred embodiment uses a peristaltic pump which is especially well-suited for long duration infusions. The use of a syringe-type cartridge pump is allowable for situations where a higher pressure is required and where larger fluid volumes may be infused into the patient.

Control apparatus 20 has a control panel 22 by which an operator can program the control apparatus 20 to infuse predetermined amounts of each fluid solution into the patient through the catheter tube. An operator would indicate to the apparatus 20 the quantity of each fluid to be pumped per unit time through the catheter tube. The apparatus 20 then computes the required pump speed and displays this information to the operator. The operator sets the pump 40 at this speed. The programmed apparatus automatically switches the valve 10 between fluid solutions to administer the prescribed regimen.

One of the inputs into the valve 10 is a neutral solution which is used as an isolator between drug solutions thereby preventing any substantial premixing of the solutions in the catheter tube 30. The control apparatus 20 will always alternate between the neutral solution and one of the drug solutions. This is the method described in the inventors' copending patent application U.S. Ser. No. 619,846 entitled "Method for Sequential Intravenous Infusion of Multiple Fluids" sharing the same filing date and assignee as the present invention and the disclosure of which is hereby incorporated by reference herein. According to this method, the spacer solution 110 is provided for substantially isolating the different fluid solutions during intravenous administration. FIG. 6 shows a first solution 112 and a second solution 114 separated by the spacer solution 110. The solutions are carried by the catheter tube 30 through a needle and into a patient. Pump 40 keeps the fluids moving through catheter tube 30 at a predetermined rate. The spacer solution 110 must be a solution which is suitable for intravenous infusion into a patient. The spacer 110 must also be neutral with respect to each of the fluid solutions on either side of it. In other words, the spacer solution 110 must not substantially react with either the first fluid solution 112 or the second fluid solution 114 while it is traveling through the catheter tube 30 into the patient. Some solutions may react with one another over a long period of time, however, it is only necessary that there be no adverse reactions prior to the infusion.

There are a number of intravenous solutions which may be selected as the neutral spacer 110, including but not limited to saline solutions, dextrose solutions and intravenous lipid solutions. The appropriate spacer solution 110 should be selected according to a patient's needs. For example, a patient requiring nutritional supplement may receive a high concentration dextrose solution as the spacer, whereas a patient merely requiring liquids may receive a saline solution or a low concentration dextrose solution.

The volume of the spacer solution 110 affects the rate of mixing between the fluid solutions on adjoining sides of the spacer. A spacer with a low volume would have a tendency to allow the adjoining fluids to diffuse more quickly into each other. On the other hand, a spacer with a larger volume would decelerate the rate of diffusion of adjoining drug solutions into each other.

The volume of the spacer solution must be selected so as to avoid substantial mixing between the fluid solutions on either side of the spacer solution 110 in the time that the solutions are in transit within the catheter tube 30. If the diffusion rate between a fluid solution and the spacer solution 110 is rapid, the spacer solution 110 must have a greater volume to avoid mixing of the two isolated fluid solutions. Some insubstantial mixing may be allowed where the first drug solution 112 and the second drug solution 114 are relatively compatible with one another and will not react when in contact to a small extent. For more highly reactive fluid solutions, any amount of mixing would be substantial and must be prevented. Thus, the appropriate volume of spacer 110 depends on a variety of factors.

Figure 7:
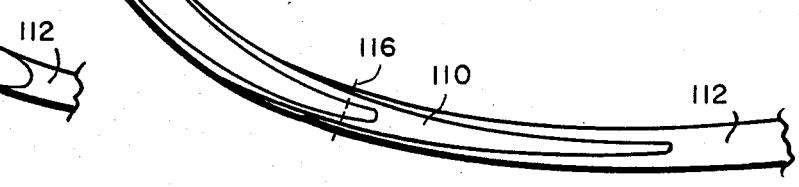
FIG. 7 is a cross-sectional view of the catheter tube shown in FIG. 1 after the neutral spacer solution has been pumped through a length of catheter tubing.
Figure 8:
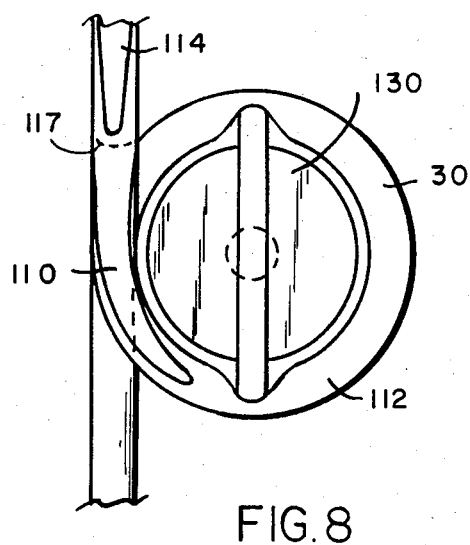
FIG. 8 is an elevational view of a peristaltic pump for use in the method and apparatus of the present invention.

Because of laminar flow which occurs during the movement of fluids through the catheter tube 30, the type of pump being used will also be determinative of the minimum volume of spacer solution 110 required to separate the first and second fluid solutions. Referring now to FIG. 7, the affects of laminar flow of fluids as they travel through the catheter tube 30 is shown. There is friction between the walls of the catheter tube 30 and the fluids which are flowing through it. This friction slows the outer layers of fluid. Thus, the fastest flowing fluid is found along the center axis of the catheter tube 30. Over a period of travel through the tube the spacer solution 110 develops a convex pointed front side and a concave indented rear side. The volume of spacer solution 110 must be prescribed to be large enough so that the rear edge of the first fluid solution 112 does not substantially overlap the leading front point of fluid solution 114. A cross-section showing such an overlap is illustrated in FIG. 7 at cross-section 116. A peristaltic pump 130, illustrated in FIG. 8, operates by squeezing the catheter tube 30. If there is a cross-section 16 including the first and second fluid solutions as they reach the peristaltic pump 130, upon being squeezed by pump 130 the two solutions would be in direct contact as a result of the pump action. Therefore, it is important that when using a peristaltic pump 130 that there be a cross-section 117 maximally filled with spacer solution 110 as the spacer solution reaches the peristaltic pump 130.

Figure 9:
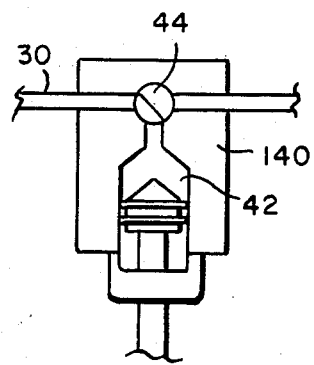
FIG. 9 is an elevational view of a syringe-type cartridge pump for use in the method and apparatus of the present invention.

A syringe-type cartridge pump 140, also known as volumetric pump, illustrated in FIG. 9 works in a different manner. The cartridge pump 140 operates by filling and emptying a chamber 42. A valve 44 rotates to switch between a filling and an emptying position. To prevent substantial mixing between fluid solution 112 and second fluid solution 114, it is again necessary to prescribe a sufficient volume of spacer solution 110 to substantially isolate the two fluid solutions. To accomplish this, the spacer solution 110 should encompass a volume which fills a cylindrical cross-section of the tube which is equal to or greater than the volume of the chamber 42. Thus, the pump chamber 42 will be prevented from substantially filling with more than one of the fluid solutions separated by the spacer 110.

It is highly important that the infused fluid solutions are not contaminated. Therefore, it is important that the valve 10 be sterile. The presently preferred embodiment employs a disposable plastic valve 10 which can withstand a conventional sterilization process.

The apparatus of the present invention individually connects a fluid solution through an input site 18 in the valve 10 with an output passageway 14 through the rotary core member 12 of the valve 10. The output passageway 14 is directly connected with the catheter tube 30. During the time interval in which the rotary core member 12 is turned to switch the connection from one solution to another, there is an instant in which both the input site 18 and the conduit 50 are exposed to the output passageway 14. Then there is an interval in which solely the neutral solution is pumped from conduit 50 through the catheter tube 30. Thus, the flow of fluid into the catheter tube 30 is continuous and is never interrupted. As the rotary core member 12 is turned to switch from conduit 50 to an input site 18, the flow of fluid into the catheter tube 30 is similarly continuous and never interrupted.

Referring now to FIGS. 2 and 3, the valve of the present invention may be described in greater detail. The valve 10 is supported in a hollow cylindrical housing 16. The housing 16 is mountable on the apparatus 20 by its mounting holes 15 and a lip 24. At the top of the valve 10, lip 24 extends outward so as to fit under ridge 25 which extends from control apparatus 20. Pins 23 projecting out of the control apparatus 20 snap into the mounting holes 15. Any conventional mounting means may be substituted for the mounting holes 15 and lip 24 as long as the valve 10 can be securely held in place and may be easily dismounted for replacement with a new sterile valve 10.

The housing 16 includes a plurality of input sites. In the preferred embodiment, there is one primary site 17 and a plurality of secondary sites 18. Each input site is a hole through the circumference of the hollow housing 16. The input site accommodates a hollow cylindrical shaft. In the case of the secondary input sites, the hollow cylindrical shafts 19 extend through the hollow housing 16 and into contact with sealing means surrounding the rotary core member 12. In the preferred embodiment, it is the circumference 13 of the rotary core member 12 which contacts and seals the cylindrical shafts 19. The ends of the shafts 19 are ground with a curve matching that of the circumference 13 of the rotary core member 12 so that the shafts lie flush against the circumference 13 to effectuate a seal. It would be possible however to provide a washer type device about the rotary core member to function as the sealing means.

The output passageway 14 extends through rotary core member 12 from an access hole 11 in the circumference 13. When the access hole 11 is not aligned with a secondary input site 18, that input site 18 will be sealed closed by the circumference 13. The primary input site 17 has a shaft 21 which does not extend to the sealing means on the rotary core member 12. Thus, access is always maintained between the primary input site 17 and a conduit 50 which surrounds the rotary core member 12. In the presently preferred embodiment, the conduit 50 is formed by the rotary core member 12 itself. The rotary core member 12 is spool-shaped to form the channel-like conduit 50 about its circumference. The conduit 50 is formed with circumference 13 as the floor and sidewalls extending from the planar surface ends of the core member 12. The conduit 50 is wider than the outer diameter of the hollow cylindrical shafts 19. Thus, as shown in FIG. 3, the conduit 50 extends around each of the secondary input sites. This enables the neutral solution which is fed through the primary input site 17 to fill the conduit 50 all the way around the rotary core member 12.

The conduit 50 simplifies the sequential switching operation of valve 10. Since treatments involve a plurality of drugs, it is desirable to avoid substantial mixing of the drugs in the catheter tube 30. To accomplish this, the neutral solution is accessed after each use of a drug solution. The conduit 50 provides access to the neutral solution between adjacent secondary input sites 18. Thus, the core member 12 can rotate directly from one solution to another and still access neutral solution in between. This construction also promotes protection against air bubbles in the line. The access hole 11 is made wider than the walls of the hollow shafts 19 so that fluid can be continuously pulled through the catheter tube 30. As the access hole 11 is moved out of direct alignment with a secondary input site 18, it will be instantaneously exposed to solution from the input site 18 and from the conduit 50. Then it will allow passage solely of the neutral solution from the conduit 50. Thus, there will be a continuous flow of fluid which will prevent air bubbles from ever forming within the system.

At the external end of each hollow cylindrical shaft 19, there is a male luer connector for mating with a female luer connector on the polymer catheter tube bringing fluid from the intravenous fluid solution source. Any conventional connecting means may be substituted for the present male-female luer connection.

The conduit 50 carrying the neutral solution must be sealed to prevent leakage. In the presently preferred embodiment, a double seal is provided by the rotary core member 12 against the hollow cylindrical housing 16. The outer planar surfaces of the rotary core member 12 frictionally engage an inner wall of a channel 26 within the inner circumference of the hollow cylindrical housing 16. The outermost circumference of the sidewalls of the rotary core member 12 frictionally engages the floor of the channel 26 in the hollow housing 16. The snug fit of the rotary core member within the hollow housing thus functions to seal the conduit 50.

The output passageway 14 is shown in FIGS. 2 and 3. It extends from the access hole 11 in the circumference 13 of the rotary core member 12 to an output site projecting from one of the planar surfaces of the core. A catheter tube 30 makes connection with the outer projection from the core 12 to provide a path for the fluid to follow. Automatic mechanical rotation of the valve 10 is made possible by the connection of a gear 60 to the rotary core member 12. The teeth of the gear 60 mesh with the teeth of a gear 80 within the control apparatus 20 so that a motor 70 within the control apparatus may control the operation of the valve 10. The engagement of the two gears further contributes to holding the valve 10 in its mounted position on the control apparatus 20.

Referring now to FIGS. 4 and 5, the mechanics of the control apparatus 20 may be explained. A stepping motor 70 rotates a pulley 72. The pulley 72 is connected by a belt 74 to a pulley 76 on a speed reducer 78. The belt 74 thus drives the speed reducer 78. The speed reducer 78 transmits torque from the motor 70 to a gear 80 which is enmeshed with the gear 60 on the valve 10. In the presently preferred embodiment, the speed reducer uses a ratio of 48 to 1. In reducing the speed, the speed reducer 78 effectively increases the torque which is applied to the gear 60 on the valve 10. The increased torque enables the rotary core member 12 to turn against the friction from the hollow housing. Any conventional means of speed reduction may be substituted for the present drive train.

The stepping motor 70 is controlled by a microprocessor located on a circuit board 90 at the rear of the control apparatus 20. Power for the microprocessor circuitry and the motor 70 is provided from a line cord 92 which is connected through a power supply 94. It is preferable to include a backup battery supply which would be automatically switched on should the power supplied over the line cord 92 be disrupted. The microprocessor circuitry also receives inputs from the control panel 22. The control panel 22 is used to program the microprocessor so that one control apparatus 20 may be used to operate the valve 10 for administering an unlimited variety of prescribed regimens.

The present invention makes possible the administration of advanced treatments using a plurality of drug solutions. The use of a greater variety of drug solutions is possible since the apparatus allows the use of a neutral solution as a spacer to prevent substantial mixing of the drug solutions in the catheter tube 30. The operation of the apparatus begins with mounting the valve 10 on the control apparatus 20. The fluid solutions are connected to the input sites 18 of the valve 10. A pump 40 is coupled to the catheter tube 30. The pump 40 is turned on and the catheter set is purged of air. The operator causes the valve 10 to turn through each input site position by pressing an appropriate button on the control panel 22. The controls and microprocessor means for implementing the controls may be provided by one skilled in the art. The operator leaves the valve 10 in each input site position until all air bubbles have been removed. The pump is then turned off.

The apparatus may now be initialized. The microprocessor memory is cleared. The volume of the neutral solution source is entered. The volume of the spacer size which is prescribed for use between the fluid solutions is entered. Then the volume of the other fluid solution sources and their prescribed rates of infusion are entered. The pumping rate or speed of pump 40 and the total volume of fluid to be infused per unit time are computed automatically and displayed to the operator on a display 26. The operator then instructs pump 40 to infuse at this speed and for this total volume. After the information has been fed into the microprocessor, thereby programming the apparatus to administer the prescribed regimen, the intravascular access needle on the catheter tube 30 is inserted into the patient and the pump 40 and control apparatus 20 are started.

The infusion process then proceeds automatically. The control apparatus 20 may be provided with an alarm that would sound after a calculated time period elapses which indicates that a solution is in need of refilling. A nurse would stop the pump and press a pause button on the control panel 22. The fluid source would be replaced or refilled. The line is purged if necessary. The new volume of fluid is entered into the control panel 22. Any necessary changes may be made to other variables entered into the apparatus. Then the pump 40 and control apparatus 20 may be restarted.

The present invention only requires a single pump and catheter tube to deliver all of the fluid solutions to the patient. The control panel can be programmed to set the amounts of fluid solutions to be provided to the patient, thereby satisfying a physician's particularly prescribed regimen. The valve of the invention is designed to effectively seal each of the drug solutions from one another so that no undesirable precipitates or reactions occur prior to the infusion. This invention thereby advantageously expands the number of drug solutions available to physicians for use in multiple drug infusion treatments. The neutral solution may be easily accessed between the input sites of the other fluid solutions to provide a spacer between the solutions in the catheter tube 30.

The valve assembly is made of a plastic that may be sterilized by a conventional method. It may be easily mounted and dismounted from the control apparatus so that it may be replaced by a new, sterile valve as needed. The disposability of the valve enhances the integrity of the sterility of the infusion system. The apparatus of the present invention has thus made possible a new and simplified method for administering a number of drug solutions to a patient through a single catheter tube attached to a single pump, without substantially mixing the drugs in the catheter tube.

Of course, it should be understood that various changes and modifications to the preferred embodiment described above will be apparent to those skilled in the art. The valve of the present invention may be of use in a variety of applications. For example, the inputs may be attached to liquor bottles and the valve may be used to mix preprogrammed drinks, or the inputs may be attached to various chemical solutions to facilitate processing within a manufacturing environment. Furthermore, the number and position of the input sites in the hollow housing may be altered to simplify the molding process for producing the valve. These and other changes can be made without departing from the spirit and the scope of the invention and without diminishing its attendant advantages. It is therefore intended that such changes and modifications be covered by the following claims.

We claim:

1. A valve demountable on a control apparatus for automatically providing selective communication between one of a plurality of available fluid sources and a catheter tube, the valve comprising:
   a hollow cylindrical housing having a plurality of input sites for connection with said fluid sources;
   a core member, rotatably engaged within said housing, having a planar surface on each end and an output passageway extending through said core member from an access hole in a circumference of said core member to an output hole in one of said planar surfaces connected to said catheter tube, said circumference of said core member sealing said input sites such that fluid is prevented from escaping from said input sites except when said access hole is aligned with one of said input sites to provide communication between said input site and said output passageway;
   conduit means for directing fluid from one of said input sites around said remaining input sites so that said fluid from said one of said input sites is in communication with said access hole whenever said access hole is positioned between two adjacent input sites; and
   gear means coupled to said core member for transmitting rotational movement from said control apparatus to said core member.

2. The valve of claim 1 wherein said housing, said gear means and said core member are comprised of a sterilizable plastic material.

3. A valve for providing selective communication between any one of a plurality of available fluids and an output tube, the valve comprising:
   a hollow cylindrical housing having a primary input site and a plurality of secondary input sites;
   a core member, disposed within said housing, having an output passageway and a first means for sealing;
   said first sealing means having an access hole in communication with said output passageway and being rotatably engaged with said housing to prevent any fluid from escaping from any of said secondary input sites except when said access hole is aligned with one of said secondary input sites to provide communication between said one of said secondary input sites and said output passageway;
   conduit means for directing fluid from said primary input site around said secondary input sites so that said fluid from said primary input site is in communication with said access hole whenever said access hole is positioned between two adjacent secondary input sites.

4. The valve of claim 3 further comprising a drive member coupled to said core member for transmitting rotational movement to said sealing means.

5. The valve of claim 4 wherein said drive member comprises a gear.

6. The valve of claim 4 wherein said housing, said core member, said drive member and said sealing means are comprised of a sterilizable plastic material.

7. The valve of claim 4 further comprising second sealing means between said housing and said core member for sealing fluids within said conduit means.

8. The valve of claim 3 wherein said secondary input sites comprise hollow cylindrical shafts extending from said housing toward said core member to contact flush against said first sealing means.

9. The valve of claim 4 wherein said conduit means is circumferentially formed around said core member between said sealing means and said housing.

10. A valve for providing selective communication between any one of a plurality of available fluids and an output tube, the valve comprising:
    a hollow cylindrical housing having a primary input site and a plurality of secondary input sites, each of said secondary input sites having a hollow cylindrical shaft extending into said housing;
    a cylindrical core member rotatable within said housing having flange means extending radially from its circumference and a planar surface on each end, said flange means, said housing and the circumference of said core member forming a conduit in communication with said primary input site, said conduit being wider than the outer diameter of each of said cylindrical shafts and said core member being disposed within said housing such that said cylindrical shafts lie flush against said core member to seal said secondary input sites;
    an output passageway within said core member, accessible through an access hole in the circumference of said core member, said passageway extending through said core member and out through a projection from one of said planar surfaces of said core member; and
    a drive member, for rotating said core member to selectively align the access hole of said output passageway with any of said secondary input sites or with said conduit to communicate fluid from one of said input sites or from said conduit into said output passageway.

11. The valve of claim 10 wherein said drive member comprises a gear.

12. The valve of claim 10 wherein said access hole is wide enough to prevent interruption of fluid flow into said output passageway when said core member is rotating said access hole between said conduit and one of said secondary input sites.

13. A method for administering multiple fluid solutions to a patient, said method comprising:
    providing a sterile valve that provides continuous communication between an output and at least one of a plurality of inputs;
    connecting a neutral solution to one input of said valve;
    connecting each of said multiple fluid solutions to different inputs of said valve;
    connecting a catheter tube between the output of said valve and said patient;
    coupling a pump to said catheter tube;
    operating said pump at a predetermined speed;
    using an electronic processor to alternately switch said valve between the input connected to said neutral solution and one of said other plurality of inputs at predetermined time intervals, said neutral solution being provided between said fluid solutions to prevent said fluid solutions from substantially mixing in said catheter tube.

14. A method for administering a plurality of fluid solutions to a patient, said method comprising;
    providing a sterile valve including a cylindrical housing having a primary input and a plurality of secondary inputs, a core member, disposed within said housing, having an output passageway with an access hole through the circumference of said core member, the circumference sealing closed the secondary input when they are not aligned with the access hole of the output passageway, and a conduit, wherein said conduit directs fluid from said primary input around said secondary inputs so that said fluid from said primary input is in communication with said output passageway whenever said access hole is positioned between two adjacent secondary inputs;

individually connecting said plurality of fluid solutions to any of said secondary inputs;

connecting a neutral solution to said primary input;

connecting a catheter tube between the output passageway of said valve and said patient;

coupling a pump to said catheter tube;

operating said pump at a predetermined speed;

rotating said core member to alternately switch the output passageway of said valve into communication with said primary input and with one of said secondary inputs at predetermined time intervals, said neutral solution being provided between each fluid solution to prevent any of said fluid solutions from substantially mixing with another fluid solution in said catheter tube.

15. The method of claim 14 wherein said switching is performed automatically by preprogrammed electronic processor means.

16. The method of claim 14 wherein said pump comprises a peristaltic pump.

17. The method of claim 14 wherein said pump comprises a syringe-type cartridge pump.

18. An apparatus for administering multiple drug infusions comprising:

(a) a demountable valve including:

a hollow cylindrical housing having a primary input site and a pluraltiy of secondary input sites;

a core member, disposed within said housing, having an output passageway and a first means for sealing;

said first sealing means having an access hole in communication with said output passageway and being rotatably engaged with said housing to prevent any fluid from escaping from any of said secondary input sites except when said access hole is aligned with one of said secondary input sites to provide communication between said one of said secondary input sites and said output passageway;

conduit means for directing fluid from said primary input site around said secondary input sites so that said fluid from said primary input site is in communication with said access hole whenever said access hole is positioned between two adjacent secondary input sites; and a drive member, connected to said core member, for rotating said core member to selectively align said access hole with any of said secondary input sites or with said conduit means to communicate fluid from said input site or from said conduit means into said output passageway;

(b) motor;

(c) drive means coupled to said motor engageable with said drive member; and (d) microprocessor means for controlling said motor to selectively communicate fluids from said input sites through said output passageway for predetermined time intervals in a predetermined sequence.

19. The apparatus of claim 18 wherein said microprocessor means includes means for controlling said motor to communicate fluids through said output passageway in a sequence alternating between fluid from said conduit means and fluid from any of said secondary input sites.

20. The apparatus of claim 18 further comprising a catheter tube in communication with said output passageway and a pump coupled to said catheter tube for causing fluids to flow from said valve through said catheter tube at a predetermined rate.

21. The apparatus of claim 20 wherein said pump comprises a peristaltic pump.

22. The apparatus of claim 20 wherein said pump comprises a syringe-type cartridge pump.

23. The apparatus of claim 18 wherein said drive member in said valve comprises a gear.

24. The apparatus of claim 18 wherein communication of fluid through said access hole is not interrupted by rotation of said core member.

25. The apparatus of claim 18 further comprising means for causing an alarm prior to exhausting a source of fluid supplying one of said input sites.

* * * * *

UNITED STATES PATENT AND TRADEMARK OFFICE
CERTIFICATE OF CORRECTION

PATENT NO. : 4,604,093

DATED : August 5, 1986

INVENTOR(S) : Brown et al.

It is certified that error appears in the above-identified patent and that said Letters Patent is hereby corrected as shown below: On the Title Page:

[57] ABSTRACT, line 5: delete "pasageway", insert --passage--
Col. 9, line 62: delete "claim 4", insert --claim 3--
Col. 10, line 1: delete "claim 4", insert --claim 3--
Col. 11, line 37: delete "pluraltiy", insert --plurality--

Signed and Sealed this

Twenty-fourth Day of March, 1987

Attest:

DONALD J. QUIGG

Attesting Officer

Commissioner of Patents and Trademarks